United States Patent
Hoornaert et al.

(10) Patent No.: US 10,172,575 B2
(45) Date of Patent: Jan. 8, 2019

(54) PROTECTION SYSTEM FOR PROTECTING A PERSON AGAINST X-RAY SCATTER RADIATION

(71) Applicant: KONINKLIJKE PHILIPS N.V., Eindhoven (NL)

(72) Inventors: Bart Pierre Antoine Jozef Hoornaert, Eindhoven (NL); Johan Juliana Dries, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 15/510,026

(22) PCT Filed: Sep. 15, 2015

(86) PCT No.: PCT/EP2015/071103
§ 371 (c)(1),
(2) Date: Mar. 9, 2017

(87) PCT Pub. No.: WO2016/041966
PCT Pub. Date: Mar. 24, 2016

(65) Prior Publication Data
US 2017/0258417 A1     Sep. 14, 2017

(30) Foreign Application Priority Data
Sep. 16, 2014 (EP) .................................. 14184961

(51) Int. Cl.
*A61B 6/10* (2006.01)
*A61B 6/00* (2006.01)

(52) U.S. Cl.
CPC .............. *A61B 6/107* (2013.01); *A61B 6/547* (2013.01)

(58) Field of Classification Search
CPC ................................. A61B 6/107; A61B 6/547
USPC .......... 250/505.1, 515.1, 516.1, 517.1, 519.1
See application file for complete search history.

(56) References Cited

U.S. PATENT DOCUMENTS

| | | |
|---|---|---|
| 2006/0181424 A1 | 8/2006 | Graves |
| 2007/0297572 A1 | 12/2007 | Moritake |
| 2008/0103834 A1 | 5/2008 | Reiner |
| 2008/0241805 A1 | 10/2008 | Schantz |

(Continued)

FOREIGN PATENT DOCUMENTS

| | | |
|---|---|---|
| DE | 102011006567 A1 | 10/2012 |
| JP | 20005253689 A | 9/2005 |

(Continued)

*Primary Examiner* — Nicole Ippolito

(57) ABSTRACT

The invention relates to a protection system (10) and a method for protecting a staff member (6) against X-ray scatter radiation, an X-ray system and a computer readable medium having stored a computer program element for controlling such system. The protection system (10) comprises a location unit (20), and a determination unit (30). The location unit (20) is configured to detect the position of a shielding device (3) and the position of the staff member (6) to be protected. The determination unit (30) is configured to determine an origin (5) of potential X-ray scatter radiation and to determine if the shielding device (3) is positioned to protect the staff member (6) to be protected based on the origin (5) of potential X-ray scatter radiation, the position of the shielding device (3) and the position of the staff member (6).

15 Claims, 3 Drawing Sheets

(56) References Cited

U.S. PATENT DOCUMENTS

| | | | |
|---|---|---|---|
| 2009/0110146 A1* | 4/2009 | Sliski | A61N 5/10 378/65 |
| 2009/0166540 A1* | 7/2009 | Peng | G01T 3/00 250/362 |
| 2010/0084586 A1* | 4/2010 | Teodorescu | G21F 3/00 250/516.1 |
| 2012/0075061 A1 | 3/2012 | Barnes | |
| 2013/0124227 A1 | 5/2013 | Ellis | |
| 2016/0249869 A1* | 9/2016 | Papalazarou | A61B 6/027 378/62 |
| 2017/0143286 A1* | 5/2017 | Exelmans | A61B 6/4233 |

FOREIGN PATENT DOCUMENTS

| | | |
|---|---|---|
| JP | 2009213709 A | 9/2009 |
| JP | 2013128511 A | 7/2013 |
| JP | 2013255741 A | 12/2013 |
| WO | 2008135906 A2 | 11/2008 |
| WO | 2014055885 A1 | 4/2014 |
| WO | 2015063191 A1 | 5/2015 |

\* cited by examiner under 35 U.S.C. § 371 of International Application No. PCT/EP2015/071103, filed on Sep. 15, 2015, which claims the benefit of European Patent Application No. 14184961.2, filed on Sep. 16, 2014. These applications are hereby incorporated by reference herein.

PROTECTION SYSTEM FOR PROTECTING A PERSON AGAINST X-RAY SCATTER RADIATION

CROSS-REFERENCE TO PRIOR APPLICATIONS

This application is the U.S. National Phase application under 35 U.S.C. § 371 of International Application No. PCT/EP2015/071103, filed on Sep. 15, 2015, which claims the benefit of European Patent Application No. 14184961.2, filed on Sep. 16, 2014. These applications are hereby incorporated by reference herein.

FIELD OF THE INVENTION

The invention relates to a protection system for protecting a person against X-ray scatter radiation, an X-ray system, a method for protecting a person against X-ray scatter radiation, and a computer program element for controlling such device and a computer readable medium having stored such computer program element.

BACKGROUND OF THE INVENTION

EP 2 147 333 A2 discloses a dose awareness indication device for determining an individual dose data of a staff member during a type of diagnostic or interventional X-ray examination of an object of interest with an examination apparatus.

During interventional procedures carried out while acquiring X-ray images of the patient, staff members may be subjected to harmful scatter radiation, in particular X-ray radiation that is being scattered by the patient undergoing the procedure.

Protection from such scatter radiation can be achieved in many ways: shielding devices (e.g. radiation safety glasses) may be in the room, behind which a staff member is "in the shade" of the scatter radiation; in a similar way one can stand "behind" another staff member, or even be "protected" by the patient. Taking enough distance from the scatter source can also have enough effect.

However, today no means are provided to guarantee that at least one of these protection mechanisms is in place for everyone. As a result, everybody is required to wear heavy, cumbersome lead aprons during the complete radiation procedure.

SUMMARY OF THE INVENTION

Hence, there may be a need to provide an improved protection system for protecting a person against X-ray scatter radiation, which facilitates working for the person.

The problem of the present invention is solved by the subject-matters of the independent claims, wherein further embodiments are incorporated in the dependent claims. It should be noted that the aspects of the invention described in the following apply also to the protection system for protecting a person against X-ray scatter radiation, the X-ray system, the method for protecting a person against X-ray scatter radiation, the computer program element, and the computer readable medium.

According to the present invention, a protection system for protecting a staff member against X-ray scatter radiation is presented. The protection system comprises a location unit and a determination unit. The location unit is configured to detect the position of a shielding device and the position of the person to be protected. The determination unit is configured to determine an origin of potential X-ray scatter radiation. The determination unit is further configured to determine if the shielding device is positioned to protect the person to be protected based on the origin of potential X-ray scatter radiation, the position of the shielding device and the position of the person to be protected.

Within the context of the invention, a "person to be protected" from scatter radiation is a medical staff member, in particular a member of a medical staff being present during an interventional X-ray procedure.

In other words, the protection system locates only the positions of the origin of potential X-ray scatter radiation, the shielding device and the person to be protected. The 2D positions are thereby sufficient, but can be extended to 3D positions. Then, the protection system determines based on this information if the surface of the person is fully free and protected from scatter radiation or if at least a part of the person's body is subjected to scatter radiation in case a radiation source is switched on. In other words, the protection system determines binary if the person is completely safe or not.

Thereby, an interventional staff member does not need to wear heavy, cumbersome personal shielding devices, as e.g. a lead apron during the complete radiation procedure. The protection system ensures that the person is protected even without a lead apron. This makes life and work much easier for the person to be protected.

In an example, the shielding device is a wall, a curtain, a moveable shield, a fixed shield, an element of an X-ray apparatus, another person or the like. The shielding device may still be an apron.

In an example, the origin of X-ray scatter radiation is a patient subject to incident X-ray radiation, for example a patient undergoing a medical intervention during which X-ray images are being acquired in order to support the intervention.

The mere knowledge of the origin of the scatter radiation is sufficient for the invention. The protection system only differs between the two conditions that the X-ray radiation is switched off or on. However, also the distance between radiation source and the person to be protected, the strength of the radiation source or the like can be used to determine if the shielding device is positioned to fully protect the person to be protected. Also a model of the X-ray scatter radiation can be used as basis for the determination if the shielding device is sufficiently positioned.

In an example, the X-ray scatter radiation can also be or can be replaced by X-ray radiation or any other kind of radiation.

In an example, the location unit comprises a layout or model of a room, in which the person to be protected is located. The location unit can also comprise a layout or model of a safety zone or a predefined region of this room. The layout or model can comprise e.g. a position of a fixed shielding device.

In an example, the location unit comprises at least a sensor, as e.g. a position, motion and/or rotation sensor to detect the position of the shielding device. For example, rotation sensors can be added to each pivot point of a pivotable shielding device. The position of the sensor can be added to the determination unit's room model.

In an example, the location unit comprises a reference point and a location tag, preferably a Real-Time Locating System (RTLS) tag. RTLS can be used to automatically identify and track the location of objects or people in real time within a room or building. The location tag can be used instead or together with above described sensor. Wireless RTLS tags may be attached to objects or worn by people. At least one fixed reference point receives wireless signals from the location tags to determine their location. The location tags and the fixed reference points can be transmitters, receivers, or both. The communication between reference point and a location tag can be made e.g. by radio frequency, optical, infrared, acoustic, ultrasound technology or the like or combinations thereof. The location unit may comprise a Wi-Fi access point and a small, long-lasting, battery-powered Wi-Fi tag. The location unit may be a real time location unit with e.g. a location accuracy from 1 mm up to 100 mm and coverage from 5 m up to a few hundred meters. The location unit may permit hundreds of tags to be tracked in all directions.

In other words, an improved system for dose protection for interventional staff is provided. Staff members and protective devices may be provided with RTLS tags, i.e. Wi-Fi tags that allow location tracking. The system determines, e.g. in real-time, the position of the plurality of location tags in the interventional room and couples this information to information concerning the scatter radiation distribution.

As a result, the location unit can be configured to detect the position of the shielding device from the layout or model, from the sensor, from the location tag and/or the like.

This invention enables to estimate a priori the radiation safety risk of every member of the staff during the X-ray examination. This allows calculating for each staff member a risk of scatter radiation and proposing suitable protection means. Via an awareness/guidance instructions related to an adequate use of an available X-ray scatter shielding device, a situation is created in which wearing lead aprons can be reduced or eliminated.

In an example, the location unit comprises a first location tag to be arranged at the person to be protected. The position of the shielding device can be taken from a room model and/or a second location tag to be arranged at the shielding device. Via location tagging of the staff member to be protected, it can be predicted whether this person is already protected properly from X-ray scatter radiation thanks to the X-ray shielding device or not. The staff members to be protected can be positioned in the shade of shielding devices, colleagues and the like or they can be positioned favorably in terms of the scatter directions or in terms of distance to the radiation source. For example, a staff member with no lead apron, but at a sufficient distance, could be considered to be in a safe position when a radiation run would be made.

The location of all staff members can also be monitored in real-time via location tags. If the shielding device is a personal shielding device, as e.g. an apron, the location tag on the shielding device can be used to determine whether the shielding device is actually used. For example, if a staff member needs to wear a lead apron, but no lead apron is positioned approximately at the same location as the person, a warning should be given.

In an example, the location unit further comprises a third location tag to be arranged at the shielding device to provide information on the size, shape and/or spatial orientation of the shielding device based on the positions of the second and third location tags. In other words, via location tagging the size, shape and/or spatial orientation of the shielding device can be measured, and the effect on the scatter radiation distribution in the examination room can be modeled. The two location tags can be arranged at two opposite or diagonal ends or corners of the shielding device.

In a further example, the location unit further comprises a fourth location tag to be arranged at the person to be protected to provide information on the spatial orientation of the person to be protected based on the relative positions of the first and fourth location tags. The two location tags can for example be arranged at two opposite ends of the person.

In an example, the location unit further comprises an information tag to be arranged at the shielding device to provide information on the type, size, shape and/or thickness of the shielding device. Thereby, the worn shielding device can be different for every individual staff member. Staff members can decide how much lead protection they want to wear (no lead aprons, thinner lead aprons, single layer, only lower part of lead apron, only on the front, not at the back, etc.). Instead of using a separate information tag, this function can also be integrated into the RTLS location tag. The RTLS location tag can then have a certain identification number or string which can be coupled to a specification type of the shielding device. In this way one tag can be enough to provide info on type, dimensions, thickness, etc.

In an example, the protection system for protecting a person against X-ray scatter radiation further comprises a control unit configured to limit and/or prevent an operating of an X-ray source in case the shielding device is not positioned to protect the person to be protected. Via automatically disabling the X-ray production in case of unsafe situations, lead-apron-free work by the staff is further enhanced. It is also possible to allow only a limited set of reduced X-ray techniques (on a real-time basis) depending on the estimated safety of the complete staff. For example, an X-ray controlling person wears a lead apron, but other staff members do not. As long as all other staff members are protected by shielding devices and are impossible to be irradiated by the scatter of the patient (given the X-ray systems geometry in terms of tube and detector positioning), the protection system will enable X-ray, and the X-ray controlling person can actually push a start button and X-ray will be generated. When however, at least one of the staff members (not protected by a lead apron) is not within or leaves a zone "in the shade" of a shielding device, the protection system will disable X-ray. This means the protection system stops the X-ray run even when the X-ray controlling person holds the start button or simply refuses to start a new X-ray run when requested to.

In an example, the control unit is further configured to control a movement of the shielding device. Motorized shielding devices can then be positioned adequately.

In an example, the protection system for protecting a person against X-ray scatter radiation further comprises an output unit configured to output instructions to re-arrange the shielding device and/or the person to be protected to achieve a protection of the person to be protected. These instructions can be awareness/guidance indications related to the usage and positioning of shielding devices as e.g. "lower the lead glass near the table a few cm" or to the staff as e.g. "if the nurse takes more distance a low radiation level will be allowed, for a higher radiation level, the nurse should find protection behind shielding device A". These instructions can also be a binary visual, auditory or other signal to indicate if the at least one person is unprotected.

In an example, the protection system for protecting a person against X-ray scatter radiation further comprises a scatter model unit configured to model a scatter radiation distribution as further input for the determination unit. The absolute scatter radiation levels may depend on geometrical parameters (angle of irradiation, etc.) and on technique factors (X-ray beam quality, X-ray intensity, use of filters, etc.). These technique factors can already be estimated prior the next irradiation event to happen to speed up. The scatter model unit can also be configured to adapt the model of the scatter radiation distribution by the positions of the shielding device(s) and person(s).

In an example, the protection system for protecting a person against X-ray scatter radiation further comprises a real-time dose monitoring unit configured to monitor the scatter radiation influencing the person to be protected. The dose monitoring unit can be linked to a personal dose meter or tag. Thereby, a correct functioning of the system can be verified and the received dose can be measured. Via dose monitoring, also the accurateness of the predicted safety can be checked. Such monitoring can be used to give feedback to the prediction part in order to improve the quality and to e.g. reduce safety margins. It can also interfere and e.g. lower or stop an X-ray run in case a staff member becomes inadequately shielded.

According to the present invention, also an X-ray system is presented. The X-ray system comprises an X-ray source, a shielding device and a protection system as described above for protecting a person against a scatter portion of the X-ray radiation. The X-ray source is configured to provide X-ray radiation. The shielding device may be one of the group of a wall, a curtain, a moveable shield, a fixed shield, an apron, an element of an X-ray apparatus or a medical staff member. The protection system comprises a location unit and a determination unit. The location unit may comprise a reference point and a location tag, preferably a RTLS tag.

According to the present invention, also a method for protecting a person against X-ray scatter radiation is presented. It comprises the following steps, not necessarily in this order:

detecting a position of a shielding device and a position of a person to be protected, determining an origin of potential X-ray scatter radiation, and determining if the shielding device is positioned to protect the person to be protected based on the origin of potential X-ray scatter radiation, the position of the shielding device and the position of the person to be protected.

The position detection may be achieved by a location unit comprising a reference point and a location tag, preferably a RTLS tag. The origin of X-ray scatter radiation may be a patient to be examined by X-ray radiation. The protection system determines based on the positions of the origin of potential X-ray scatter radiation, the shielding device and the person to be protected if the surface of the person is fully free and protected from scatter radiation or if at least a part of the person's body is subjected to scatter radiation in case a radiation source is switched on. In other words, the protection system determines binary if the person is completely safe or not.

According to the present invention, also a computer program element is presented, wherein the computer program element comprises program code means for causing a protection system for protecting a person against X-ray scatter radiation as defined in the independent device claim to carry out the steps of the method for protecting a person against X-ray scatter radiation when the computer program is run on a computer controlling the protection system for protecting a person against X-ray scatter radiation.

It shall be understood that the protection system for protecting a person against X-ray scatter radiation, the X-ray system, the method for protecting a person against X-ray scatter radiation, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
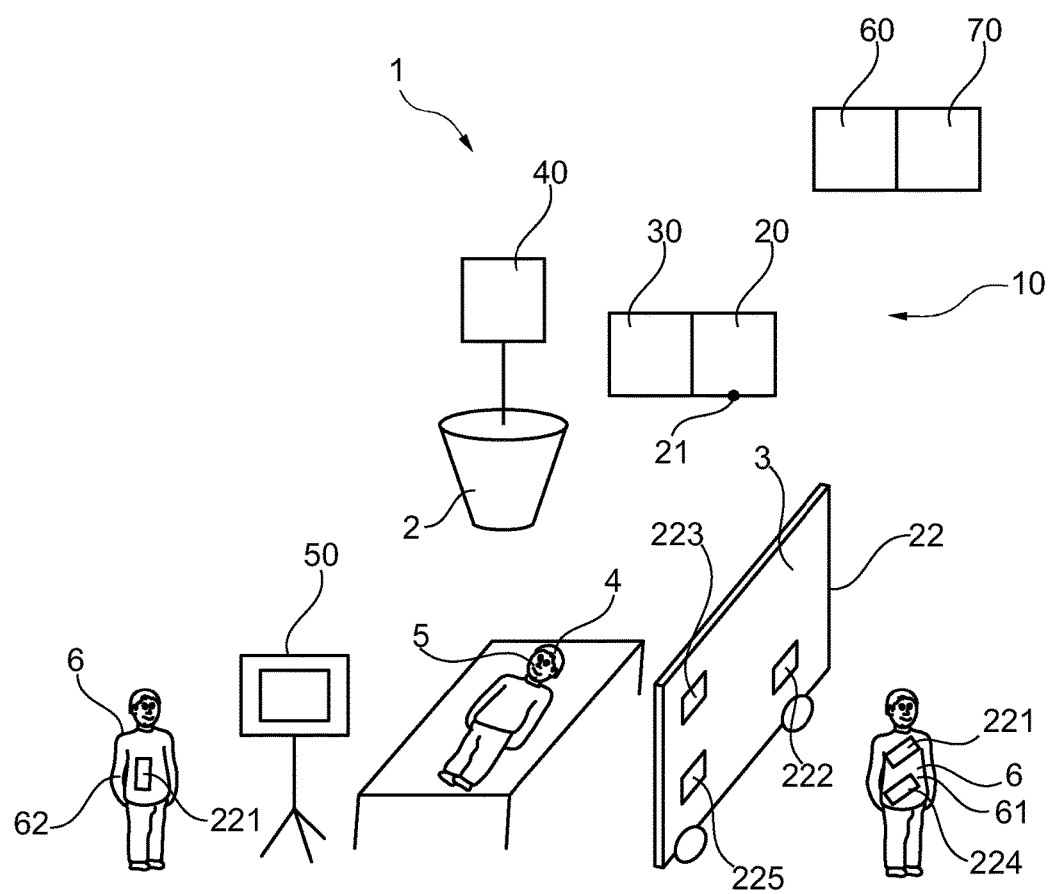
FIG. 1 shows a schematic drawing of an example of an X-ray system according to the invention.

FIG. 1 shows schematically and exemplarily an embodiment of an X-ray system 1 according to the invention. The X-ray system 1 comprises an X-ray source 2, at least one shielding device 3 and a protection system 10 for protecting persons 6, in particular medical staff members 61, 62, against a scatter portion of the X-ray radiation. The X-ray source 2 provides X-ray radiation. The shielding device 3 is here a moveable wall, but may be also at least one of the group of a fixed wall, a curtain, a moveable shield, a fixed shield, an apron, an element of an X-ray apparatus or a medical staff member.

The protection system 10 comprises a location unit 20 and a determination unit 30. The location unit 20 detects the position of the shielding device 3 and the position of the person 6 to be protected. The location unit 20 here therefore comprises a reference point 21 and a location tag 22, here a wireless RTLS tag. The determination unit 30 determines an origin 5 of potential X-ray scatter radiation, which is here a patient 4 to be examined. The determination unit 30 further determines if the shielding device 3 is positioned to protect the person 6 to be protected based on the origin 5 of potential X-ray scatter radiation, the position of the shielding device 3 and the position of the person 6 to be protected.

The location unit 20 of the protection system 10 for protecting a person 6 against X-ray scatter radiation comprises in this example a first location tag 221 arranged at each person 6 to be protected and a second location tag 222 arranged at the shielding device 3. Via location tagging of the persons, here the staff members, it can be predicted whether the staff is already protected properly from X-ray scatter radiation thanks to the X-ray shielding device 3 or not.

The location unit 20 further comprises in this example a third location tag 223 arranged at the shielding device 3 to provide information on the size, shape and spatial orientation of the shielding device 3 based on the positions of the second and third location tags. The second and third location tags 222, 223 are arranged at two opposite ends of the shielding device 3. Via location tagging of the second and third location tags 222, 223, the size, shape and/or spatial orientation of the shielding device 3 can be measured.

The location unit 20 further comprises in this example a fourth location tag 224 arranged at the person 6 to be protected to provide information on the spatial orientation of the person 6 to be protected based on the positions of the first and fourth location tags 221, 224. The first and fourth location tags 221, 224 are arranged spaced apart from each other at the person 6.

The location unit 20 further comprises in this example an information tag 225 arranged at the shielding device 3 to provide information on the type, size, shape and thickness of the shielding device 3 to the protection system 10. Thereby, the worn shielding device 3 can be different for every individual staff member.

The protection system 10 for protecting a person 6 against X-ray scatter radiation may further comprise a control unit 40 connected to the X-ray source 2 to limit and/or prevent an operating of the X-ray source 2 in case the shielding device 3 is not positioned to protect all persons 6 to be protected. Via automatically disabling the X-ray production in case of unsafe situations, lead-apron-free work by the staff is further enhanced. It is also possible to allow only a limited set of reduced X-ray techniques depending on the estimated safety of the complete staff. For example, a first staff member 61 is hidden behind the shielding device 3, but a second staff member 62 is not. As long as all staff members are protected by the shielding device 3 and are impossible to be irradiated by the scatter of the patient 4 (given the X-ray system's geometry in terms of tube and detector positioning), the protection system 10 will enable X-ray, and the first staff member 61 can actually push a start button and X-ray will be generated. When however, at least one of the staff members 62 (not protected by a lead apron) is not within or leaves a zone "in the shade" of any shielding device 3, the protection system 10 will disable X-ray. This means the protection system 10 stops the X-ray run even when the first staff member 61 holds the start button or simply refuses to start a new X-ray run when requested to. The control unit 40 further controls a movement of the shielding device 3 to position it adequately.

The protection system 10 for protecting a person 6 against X-ray scatter radiation may further comprise an output unit 50 connected to the control unit 40 and outputting instructions to re-arrange the shielding device 3 and/or the person 6 to be protected to achieve a protection of the person 6 to be protected. These instructions can be a binary visual, auditory or other signal to indicate if the at least one person 6 is unprotected. These instructions can also be awareness/guidance indications related to the usage and positioning of shielding devices as e.g. "move the wall 3 cm to the left" or to the staff as e.g. "person 62 should find protection behind wall 3".

The protection system 10 for protecting a person 6 against X-ray scatter radiation may further comprise a scatter model unit 60 connected to the determination unit 30 to model a scatter radiation distribution as further input for the determination unit 30 prior the next irradiation event to happen to speed up. The scatter model unit 60 can also be configured to adapt the model of the scatter radiation distribution by the positions of the shielding device(s) 3 and person(s) 6.

The protection system 10 for protecting a person 6 against X-ray scatter radiation may further comprise a real-time dose monitoring unit 70 to monitor the scatter radiation influencing the person 6 to be protected. The dose monitoring unit 70 can be linked to a personal dose meter or tag. It can interfere and e.g. lower or stop an X-ray run in case a staff member becomes inadequately shielded.

Figure 2:
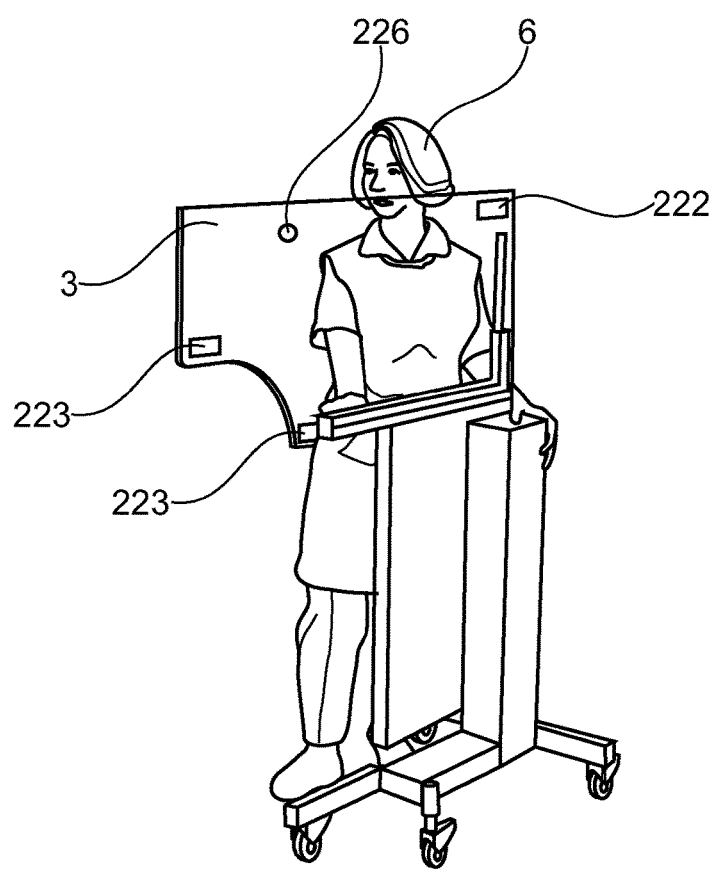
FIG. 2 shows a schematic drawing of an example of a shielding device according to the invention.

FIG. 2 shows a schematic drawing of an example of a shielding device 3 according to the invention. The shielding device 3 is a moveable and pivotable shielding device to protect a person 6. The shielding device 3 is provided with a second and two third location tags 222, 223 are arranged at opposite corners of the shielding device 3 to provide information on the size, shape and spatial orientation of the shielding device 3 to the protection system 10. The shielding device 3 is further provided with a sensor 226, which can be a position, motion and/or rotation sensor to detect the position of the shielding device 3. The position of the sensor can be added to a room model.

Figure 3:
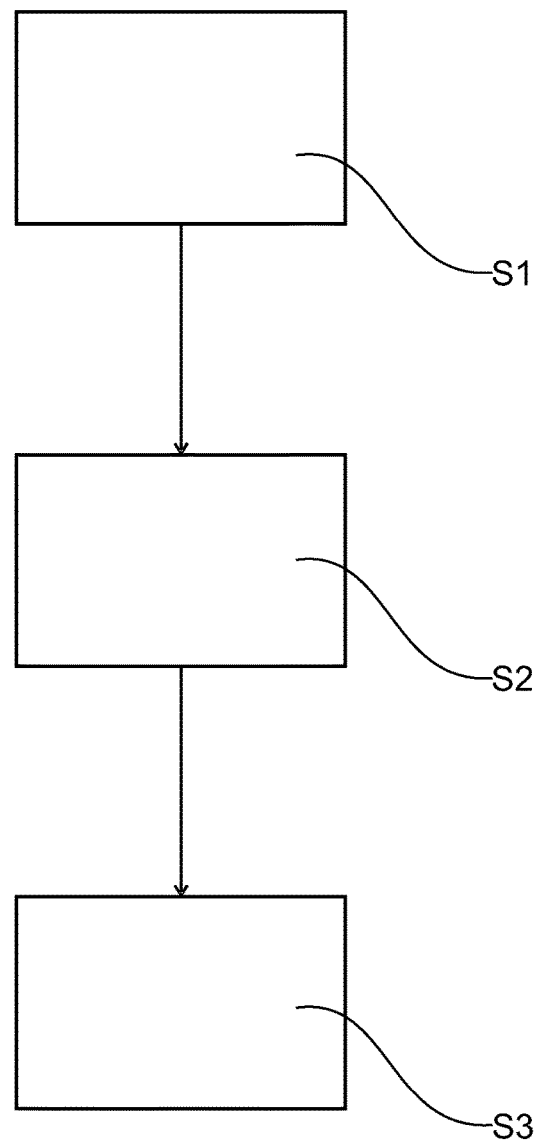
FIG. 3 shows basic steps of an example of a method for protecting a person against X-ray scatter radiation.

FIG. 3 shows a schematic overview of steps of a method for protecting a person 6 against X-ray scatter radiation. The method comprises the following steps, not necessarily in this order:

detecting a position of a shielding device 3 and a position of a person 6 to be protected.

determining an origin 5 of potential X-ray scatter radiation.

determining if the shielding device 3 is positioned to protect the person 6 to be protected based on the origin 5 of potential X-ray scatter radiation, the position of the shielding device 3 and the position of the person 6 to be protected.

The position detection is achieved by a location unit 20 comprising in this example a reference point and a RTLS tag. The origin 5 of X-ray scatter radiation is here the patient 4 to be examined by X-ray radiation. The protection system 10 determines based on the positions of the origin 5 of potential X-ray scatter radiation, the shielding device 3 and the person 6 to be protected if the surface of the person 6 is fully free and protected from scatter radiation or if at least a part of the person's body is subjected to scatter radiation in case a radiation source 2 is switched on. In other words, the protection system 10 determines binary if the person 6 is completely safe or not.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person 6 skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A protection system for protecting a staff member against X-ray scatter radiation, comprising:
   a location unit, and
   a determination unit, wherein the location unit is configured to detect the position of a shielding device and the position of the staff member to be protected,
   wherein the determination unit is configured to determine an origin of potential X-ray scatter radiation, and
   wherein the determination unit is configured to determine if the shielding device is positioned to protect the staff member based on the origin of potential X-ray scatter radiation, the position of the shielding device and the position of the staff member to be protected.

2. Protection system according to claim 1, wherein the origin of the X-ray scatter radiation is a patient subject to incident X-ray radiation.

3. Protection system according to claim 1, wherein the location unit comprises a first location tag to be arranged at the staff member to be protected and a second location tag to be arranged at the shielding device.

4. Protection system according to claim 3, wherein the location unit further comprises a third location tag to be arranged at the shielding device to provide information on the size, shape and/or spatial orientation of the shielding device based on the positions of the second and third location tags.

5. Protection system according to claim 3, wherein the location unit further comprises a fourth location tag to be arranged at the staff member to be protected to provide information on the spatial orientation of the staff member based on the relative positions of the first and fourth location tags.

6. Protection system according to claim 1, wherein the location unit further comprises an information tag to be arranged at the shielding device to provide information on the type and/or size, shape of the shielding device.

7. Protection system according to claim 1, further comprising a control unit configured to limit and/or prevent an operating of an X-ray source in case the shielding device is not positioned to protect the staff member.

8. Protection system according to claim 1, wherein the control unit is further configured to control a movement of the shielding device.

9. Protection system according to claim 1, further comprising an output unit configured to output instructions to re-arrange the shielding device and/or the staff member to be protected to achieve a protection of the staff member.

10. Protection system according to 1, further comprising a scatter model unit configured to model a scatter radiation distribution as further input for the determination unit.

11. Protection system according to 1, further comprising a real-time dose monitoring unit configured to monitor the scatter radiation influencing the staff member to be protected.

12. An X-ray system comprising a protection system according to claim 1 for protecting a staff member against a scatter portion of the X-ray radiation, an X-ray source configured to provide X-ray radiation, and a shielding device, wherein the shielding device is configured so that its position is detectable by the protection system.

13. X-ray system according to claim 12, wherein the shielding device is one of the group of a wall, a curtain, a moveable shield, a fixed shield, an apron, an element of an X-ray apparatus or a further medical staff member.

14. A method for protecting a staff member against X-ray scatter radiation, comprising the following steps:
   detecting a position of a shielding device and a position of a staff member to be protected,
   determining an origin of potential X-ray scatter radiation, and
   determining if the shielding device is positioned to protect the staff member to be protected based on the origin of potential X-ray scatter radiation, the position of the shielding device and the position of the staff member to be protected.

15. A computer readable medium embodied on a machine readable medium having stored a computer program element for controlling the protection system according to claim 1 and the X-ray system, which, when being executed by a processing unit, is adapted to perform the method steps for protecting a staff member against X-ray scatter radiation.

* * * * *